(12) United States Patent
Garcia et al.

(10) Patent No.: US 8,940,880 B2
(45) Date of Patent: Jan. 27, 2015

(54) PROCESS FOR THE PREPARATION OF 9-DEOXO-9A-HOMOERYTHROMYCIN A, MODIFIED IN THE C-4" OF THE CLADINOSE RING BY AN EPOXIDE GROUP

(75) Inventors: Rafael Garcia, Barcelona (ES); Oriol Martorell, Barcelona (ES); Albert Codony, Barcelona (ES)

(73) Assignee: Novartis AG, Basel (CH)

( * ) Notice: Subject to any disclaimer, the term of this patent is extended or adjusted under 35 U.S.C. 154(b) by 8 days.

(21) Appl. No.: 13/825,167

(22) PCT Filed: Sep. 19, 2011

(86) PCT No.: PCT/EP2011/066205
§ 371 (c)(1),
(2), (4) Date: Mar. 20, 2013

(87) PCT Pub. No.: WO2012/038372
PCT Pub. Date: Mar. 29, 2012

(65) Prior Publication Data
US 2013/0197204 A1    Aug. 1, 2013

(30) Foreign Application Priority Data
Sep. 20, 2010   (CH) ...................................... 1539/10

(51) Int. Cl.
C07H 17/00 (2006.01)
C07H 17/08 (2006.01)
C07H 19/01 (2006.01)

(52) U.S. Cl.
CPC ................ C07H 19/01 (2013.01); C07H 17/08 (2013.01)
USPC .......................................... 536/7.4; 536/18.5

(58) Field of Classification Search
CPC ....................................... C07H 17/08
USPC ........................................... 536/7.4
See application file for complete search history.

(56) References Cited

U.S. PATENT DOCUMENTS

| | | | | |
|---|---|---|---|---|
| 3,478,014 | A  * | 11/1969 | Tamburasov et al. | 536/7.4 |
| 6,825,327 | B2 * | 11/2004 | Sklavounos et al. | 536/7.4 |
| 7,410,952 | B2 * | 8/2008  | Codony et al. | 514/29 |
| 2004/0180842 | A1 * | 9/2004 | Bronk et al. | 514/28 |

FOREIGN PATENT DOCUMENTS

| | | |
|---|---|---|
| CN | 1384108 | 12/2002 |
| IT | 1246776 | 11/1994 |
| WO | 0031097 | 6/2000 |

* cited by examiner

*Primary Examiner* — Elli Peselev
(74) *Attorney, Agent, or Firm* — Ann R. Pokalsky; Dilworth & Barrese, LLP

(57) ABSTRACT

The present invention concerns a process for the preparation of the compound of formula

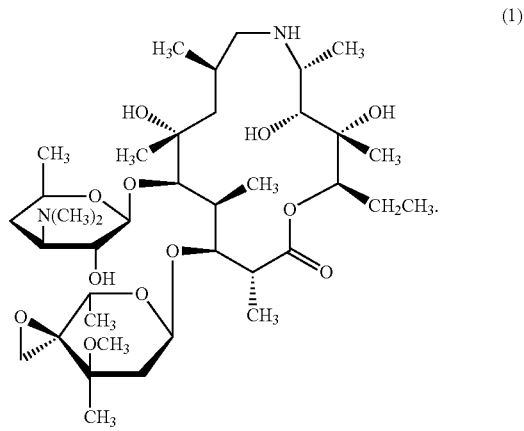

(1)

The compound of formula (1) is the key intermediate in the synthesis of some antibacterial agents of the triamilide class, such as Tulathromycin, useful to treat bacterial and protozoa infections.

12 Claims, No Drawings

PROCESS FOR THE PREPARATION OF 9-DEOXO-9A-HOMOERYTHROMYCIN A, MODIFIED IN THE C-4" OF THE CLADINOSE RING BY AN EPOXIDE GROUP

This application is a 371 application of PCT/EP2011/066205, filed Sep. 19, 2011, the contents of which are incorporated by reference herein.

The present invention relates to a novel process for the preparation of 9-deoxo-9a-aza-9a-homoerythromycin A modified in the C-4" of the cladinose ring by an epoxide group. This compound is, for example, an important intermediate of the synthesis of Tulathromycin.

BACKGROUND OF THE INVENTION

This invention relates to a novel process for the preparation of the compound of formula

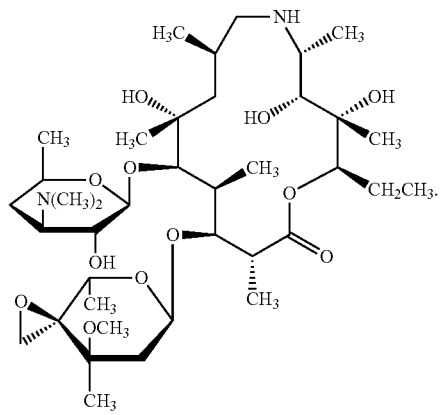

(1)

The compound is suitable to introduce a new functionality in the C-4" position of the cladinose ring of azaerythromycin A, typically a third basic amine group or other heteroatom functionality.

A further object of the invention are the novel intermediates of the process of the invention. These novel compounds may be isolated in crystalline form as stable solids with high yield and purity.

Macrolides are a well known class of antibiotics. Clarithromycin and azithromycin have been used for the treatment of human respiratory infections caused by a variety of pathogens for quite a long time. Most recently, Tulathromycin has been approved for the treatment and prevention of bacterial respiratory disease in cattle and pigs. Tulathromycin is a 15-membered azalide antibiotic of the formula

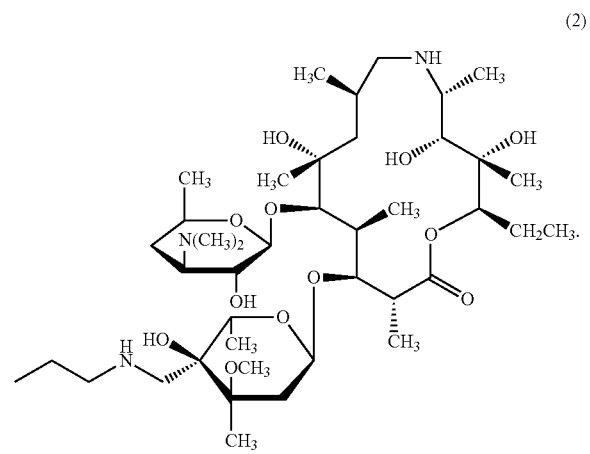

(2)

Processes for the preparation of Tulathromycin, known, for example, from in EP 0988310 or EP 1253153, use 9-deoxo-9a-aza-9a-homoerythromycin A (azaerythromycin A) as starting material. Following protection of the amino group 9a and the hydroxyl group C-2' with benzylchloroformate, the hydroxyl group in 4-position is oxidized and following deprotection converted into the epoxide of formula (1) above, which is in turn converted to Tulathromycin by reaction of the epoxide group with n-propylamine.

The main drawbacks of the known synthesis are:
(i) The use of highly toxic benzylchloroformate as protecting agent, which is known to be a human carcinogen by itself or as a consequence of the impurities usually contaminating this reagent. On the other hand, it is classified as a marine pollutant thus raising additional safety concerns specially when handling at industrial scale.
(ii) The isolation and purification of process of intermediates and the Tulathromycin requires laborious column chromatography in order to remove impurities and side products formed during the reactions.
(iii) Catalytic hydrogenation for three days is necessary to remove protective groups introduced after the oxidation step. This hydrogenation is carried out in presence of toxic class 1 metals (i.e.: Paladium) which need to be adequately removed to very low levels and not carried over into the Tulathromycin.
(iv) The instability of azalides, in particular if the nitrogen in the 9a position is not methylated, causes degradation of the 15-membered azalide backbone, as well known and documented in the literature.

Therefore, the need for an improved process for the production of Tulathromycin, which is feasible on an industrial scale does exist. It now has surprisingly been found a smooth, upscaleable synthesis for Tulathromycin and its precursor of the above formula (1) starting from erythromycin A 9-(E)-oxime instead of azaerythromycin A.

SUMMARY OF THE INVENTION

The present invention in one aspect relates to a new process for production of (2R,3S,4R,5R,8R,10R,11R,12S,13S,14R)-2-ethyl-3,4,10-trihydroxy-13-[[(3S,4S,6R,8R)-8-methoxy-4,8-dimethyl-1,5-dioxaspiro[2.5]oct-6-yl]oxy]-3,5,8,10,12,14-hexamethyl-11-[[3,4,6-trideoxy-3-(dimethylamino)-α-D-xylo-hexopyranosyl]oxy]-1-oxa-6-azacyclopenatdecane-15-one of formula (1) above comprising the steps of:
(i) protecting the hydroxyl group in the C-2' and, optionally, the C-9 oxime group of erythromycin A 9-(E)-oxime to obtain a compounds of formula

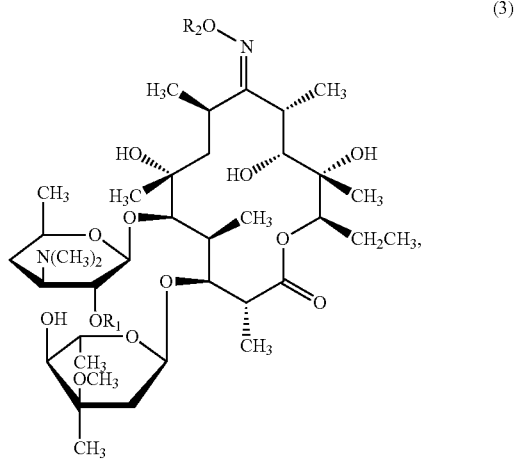

(3)

wherein $R_1$ is a hydroxyl protecting group and $R_2$ is hydrogen or an oxime protecting group;

(ii) oxidizing the compound of formula (3) in the presence of an oxidizing agent in order to obtain a compound of formula (4)

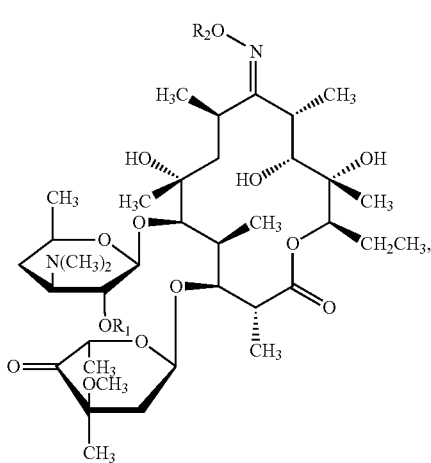

wherein $R_1$ and $R_2$ are as defined above;
(iii) converting the compound of formula (4) to the corresponding epoxide of formula (5)

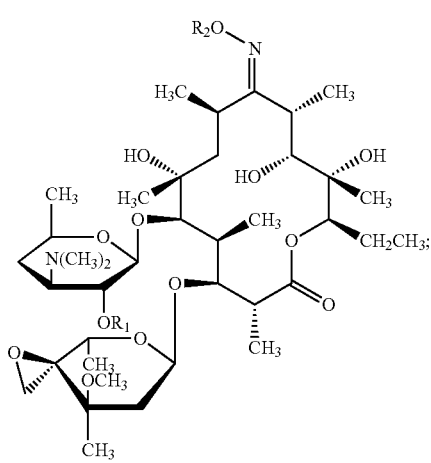

wherein $R_1$ and $R_2$ are as defined above;
(iv) removing the protecting group $R_1$ and optionally $R_2$ of the compound of formula (5) to yield the compound of formula (6)

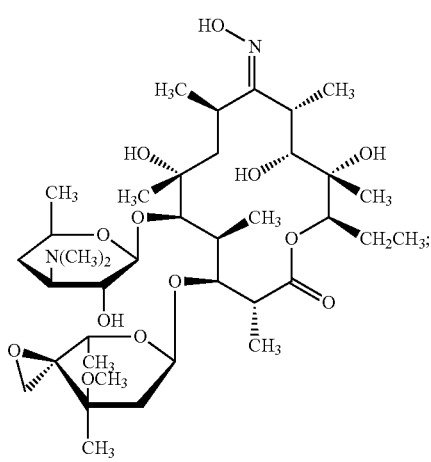

(v) subjecting the oxime of formula (6) to a Beckmann rearrangement in order to obtain the corresponding 6,9-iminoether of formula (7)

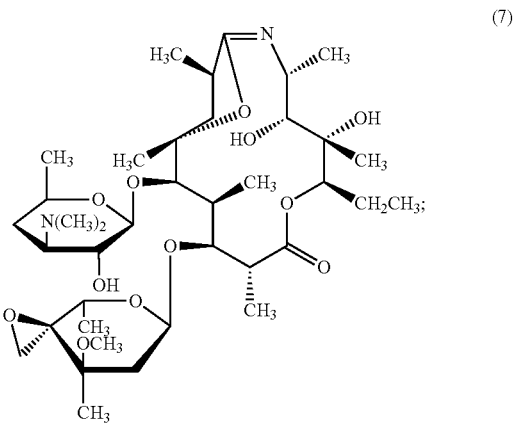

and
(vi) reducing the iminoether of formula (7) to obtain the epoxide of formula (1).

According to a further embodiment of the invention, first of all the epoxide of formula (1) is prepared according to the process as described above, and is further converted to Tulathromycin according to a method known per se, for example from EP 0988310 or EP 1253153.

Further embodiments of the invention concern the novel intermediates of formulae (4), (5), (6) and (7).

DETAILED DESCRIPTION OF THE INVENTION

Step (i) of the synthesis concerns the selective protection of the 2'-hydroxy group and, optionally, the hydroxyl group corresponding to the oxime group in the 9-position using a suitable protecting group. Suitable hydroxyl protecting groups are, for example, those referred to in T. W. Greene and P. G. M. Wuts "Protective Groups in Organic Synthesis", John Wiley & Sons, New York, 1991 together with hydroxyl protecting groups familiar to those skilled in the art. Preferably, the hydroxyl protecting groups in 2' ($R_1$) and 9 position ($R_2$) are each $C_2$-$C_4$-alkanoyl, more preferably acetyl or propionyl, and in particular acetyl.

Accordingly, $R_1$ is preferably $C_2$-$C_4$-alkanoyl, more preferably acetyl or propionyl, and in particular acetyl. $R_2$ is preferably hydrogen (H) or $C_2$-$C_4$-alkanoyl, more preferably H or acetyl or propionyl, and in particular H or acetyl.

The starting material erythromycin A 9-(E)-oxime is commercially available or may be easily prepared according to synthetic methods known per se, for example from *Tetrahedron Letters*, 1970, p. 157.

The hydroxyl group in the C-2' position and the hydroxyl group of the oxime may be protected, for example by treatment with a suitable organic acid or a derivative thereof, for example, with an acid anhydride or acid halide in a polar, aprotic solvent at about room temperature. Introduction of the preferred acetyl groups is accomplished, for example, by treatment of erythromycin A 9-(E)-oxime with about 2.5 equivalents of acetic anhydride in an polar aprotic organic solvent, for example dichloromethane, at room temperature according to the procedure described by J. Berge et. al. in WO2004/039822. An alternative solvent for this reaction is, for example, a ketone such as acetone or methyl isobutyl ketone, an ether such as methyl tert.-butyl ether, or an acetic acid ester such as ethyl acetate, isopropyl acetate or isobutyl acetate. According to a preferred embodiment, both the hydroxyl group in the C-2' position and the hydroxyl group of the oxime in 9-position are protected by acylation, in particular by acetylation, that is $R_1$ and $R_2$ are both alkanoyl, in particular acetyl.

The compounds of formula (3) may be further processed without isolation or may be crystallized from the appropriate solvent or mixture of solvents, collected by filtration and further processed with or without drying.

Oxidation of the compounds of formula (3) to the corresponding ketones of formula (4) according to step (ii) is carried out, for example, by employing commonly used oxidizing agents and processes, for example activated dimethylsulfoxide (DMSO) and related reagents and including the methods described by T. T. Tidwell in *Synthesis*, 1990, 857-870 and modifications thereof. DMSO may be activated, for example, by using trifluoroacetic anhydride, oxalyl chloride, a polyphosphoric acid, a pyridine-$SO_3$ complex or acetic anhydride. The oxidation step (ii) can be accomplished also by using Dess-Martin periodinane, metal (cromium, manganese or selenium) oxides or salts, or any other oxidant. Typical reactions conditions for the oxidation are described, for example, in EP 1253153, and include:
a) Moffat oxidation: 1-(3-dimethylaminopropyl)-3-ethylcarbodiimide and DMSO in the presence of pyridinium trifluoroacetate.
b) Swern oxidation:
(i) Oxalyl chloride and DMSO in methylene chloride followed by the addition of triethylamine.
(ii) Trifluoroacetic anhydride and DMSO in methylene chloride followed by the addition of triethylamine.

In an embodiment of the process described herein, the compound of formula (3) is oxidized to a compound of formula (4) in a medium comprising trifluoroacetic anhydride and dimethylsulfoxide and one or more polar aprotic solvents, for example methylene chloride or a THF solvent such as tetrahydrofuran or 2-methyltetrahydrofuran, at low temperature, for example between –70° C. and –60° C., followed by addition of an amine, for example N,N-diisopropylethylamine, triethylamine, N,N-diethylmethylamine, N-ethylpiperidine, N-methylpyrrolidine or 1,4-diazabicyclo[2.2.2]octane triethylamine, in particular triethylamine, while keeping the temperature.

In a further embodiment thereof, the resulting compound of formula (4) is isolated by crystallization from an appropriate solvent or mixture of solvents. If necessary an anti-solvent may be added. Preferred solvents for the crystallization of the compounds of formula (4) are polar protic and polar aprotic solvents such as alcohols, ketones or acetonitrile. Preferred anti-solvents are, for example, water, hydrocarbons and ethers. A preferred embodiment of the invention concerns a compound of formula (4), wherein $R_1$ and $R_2$ are each acetyl.

According to step (iii) of the process of the invention, the ketones of formula (4) are converted to epoxides of the formula (5), suitably by treatment with a sulfur ylide at low temperature. A preferred sulfur ylide is dimethylsulfonium methylide (i.e.: $(CH_3)_2S^+CH_2^-$).

Sulfur ylides such as dimethylsulfonium methylide are prepared by conventional methods known per se. For example, a compound $(R)_3S^+X^-$, wherein R is, for example, methyl, and X is preferably halo, $BF_4$, $PF_6$ or a sulfonate, is treated with a base acting as activating agent, for example with potassium hydroxide, potassium tert-butoxide, sodium tert-butoxide, potassium ethoxide, sodium ethoxide, sodium methoxide or potassium hexamethyldisilazide.

Typical solvents used for the reaction of the compound of formula (4) with a sulfur ylide are ethers, for example tetrahydrofuran (THF), 2-methyltetrahydrofuran, methyl tert-butyl ether, diisopropyl ether and the like, aromatic hydrocarbons, for example toluene, chlorinated aliphatic hydrocarbons, for example methylene chloride, DMSO or mixtures of one or more of the foregoing solvents. Most preferred solvents are THF or a mixture of THF and methylenechloride.

Work-up of the reaction mixture is advantageously performed by quenching, for example, with an aqueous weak acidic solution and extracting the product into a water immiscible solvent.

In a preferred embodiment, dimethylsulfonium methylide is generated by reaction of trimethylsulfonium bromide $((CH_3)_3S^+Br^-)$ with potassium tert-butoxide at a temperature below –10° C. in THF. In another preferred embodiment, a solution of the ketone of formula (4) in methylene chloride is added dropwise to the dimethylsulfonium methylide solution in THF cooled to a temperature between –60 and –80° C. to yield an epoxide of the formula (5).

In a further embodiment thereof, compound of formula (5) is isolated by crystallization from an appropriate solvent or mixture of solvents. If necessary an anti-solvent may be added. Preferred solvents for the crystallization of compounds of formula (5) are polar protic and polar aprotic solvents such as alcohols, for example methanol, ethanol, isopropanol, n-propanol, n-butanol or sec-butanol, in particular isopropanol; ketones, for example acetone, methylethylketone or methylisobutylketone, in particular acetone; and acetonitrile or mixtures thereof. Preferred anti-solvents are among others water, hydrocarbons and ethers. A preferred embodiment of the invention concerns an epoxide compound of formula (5), wherein $R_1$ and $R_2$ are each $C_2$-$C_4$-alkanoyl, in particular acetyl. A further preferred embodiment of the invention concerns a compound of formula (5), wherein $R_1$ is $C_2$-$C_4$-alkanoyl, in particular acetyl, and $R_2$ is hydrogen, which is obtainable during epoxide formation through loss of the acetyl group attached to the oxime.

Removal of protecting group(s) of the 2'-hydroxy group and the hydroxyl group corresponding to the oxime group in the 9 position, if applicable, according to step (iv) of the process of the invention is performed by processes known per se, for example, as described in T. W. Greene and P. G. M. Wuts "Protective Groups in Organic Synthesis", John Wiley & Sons, New York, 1991. In case of hydroxyl groups that are protected by esterification, cleavage is preferably carried out by alcoholysis. Preferably, the compound of formula (4) is treated with an alcohol, for example with a $C_1$-$C_4$-alkanol, more specifically with an alcohol selected from the group consisting of methanol, ethanol, n-propanol, isopropyl alcohol, tert-butyl alcohol, n-butanol or a mixture of two or more alcohols, at a temperature of, for example, from 0° C. to 100° C., preferably at 0-30° C.

According to a particularly preferred embodiment of step (iv), removal of the acetyl group(s) of the compound of formula (5) is completed by treatment with methanol at a temperature of 15-25° C. to yield the compound of formula (6) above.

In a further embodiment thereof, the compound of formula (6) is isolated by crystallization from an appropriate solvent or mixture of solvents. For example, the compound of formula (6) is isolated by distilling off the solvent used in the reaction and/or replacing it by a polar protic or polar aprotic solvent such as alcohols, ketones, acetonitrile or mixtures thereof. If necessary an anti-solvent may be added. Preferred anti-solvents are among others water, hydrocarbons and ethers.

The conversion of the compound of formula (6) to the corresponding 6,9-iminoether of the formula (7) according to step (v) is accomplished, for example, by means of a Beckmann rearrangement reaction. The Beckmann rearrangement in principle may be carried out under acidic, neutral and basic conditions. Due to the sensitivity of macrolides to acidic conditions and possible isomerization of the oxime function under basic conditions, it is, however, advisable to modify the reaction conditions.

A preferred method for effecting the ring expansion of the erythromycin A 9-oxime derivative of formula (6) by the Beckmann rearrangement involves initial O-sulfonylation of the oxime group with a sulfonic acid derivative, for example with an alkylsulfonyl halide, arylsulfonyl halide or arylsulfonic acid anhydride, in particular with an arylsulfonyl halide such as in particular p-toluenesulfonyl chloride. The intermediate oxime sulfonate thus formed is either after its previous isolation or, preferably, directly transformed into the rearranged product of formula (7). The reaction is advantageously performed in the presence of an inorganic or organic base in a suitable organic solvent, for example in a mixture of a water-soluble organic solvent and water, such as aqueous acetone, or aqueous dioxane, or in a polar organic solvent such as dichloromethane, chloroform, ethyl acetate, diethyl ether, tetrahydrofuran, toluene, acetonitrile, pyridine or a mixture of two or more of said organic solvents. Most preferred solvents are acetone or a mixture of acetone and water.

The Beckmann rearrangement reaction is preferably carried out at a pH of from 8 to 10 and at a temperature from $-10°$ C. to $10°$ C.

In a particularly preferred embodiment of the process, p-toluenesulfonyl chloride is added portionwise to a solution of the oxime of formula (6) in a mixture of acetone and water at a temperature between $0°$ C. and $5°$ C. and keeping the pH above 9.0 by addition of aqueous sodium hydroxide. Preferably, the iminoether of the formula (7) crystallizes out from the reaction mixture, and, following the addition of water and pH adjustment to 10-12, preferably 10.5-11.0, and maintenance of the temperature between, for example, $5°$ C. to $30°$ C. may be isolated by filtration.

In a further embodiment thereof, compound of formula (7) is recrystallized from an appropriate solvent or mixture of solvents. Polar protic and polar aprotic solvents such as alcohols, ketones or acetonitrile are suitable solvents to carry out the aforementioned recrystallization.

The macrocyclic imidate of formula (7) obtained according to step (v) is reduced to the epoxide of the formula (1) using a suitable reducing agent. There are two common methods available for carrying out said reduction reaction.

(a) The first one uses complex metal hydrides in an appropriate solvent system. Suitable hydride reducing agents include lithium aluminium hydride, diisobutyl aluminium hydride, sodium or potassium borohydride and sodium cyanoborohydride. Lithium aluminium hydride and diisobutyl aluminium hydride require the use of anhydrous solvents such as benzene, toluene, diethyl ether, tetrahydrofuran and dimethoxyethane, whereas sodium or potassium borohydride and sodium cyanoborohydride can be used in alcoholic solvents, for example in methanol, ethanol, isopropanol or ethyleneglycol, or in water or in mixtures of two or more of the solvents mentioned. Preferred complex metal hydrides according to the invention are sodium borohydride or potassium borohydride. Preferred solvents are methanol, ethanol, isopropanol, water, or mixtures thereof. The reduction is preferably carried out at a temperature of from $-10°$ C. to $10°$ C. and a pH of from 6.5 to 8.5.

(b) The second method uses hydrogen in the presence of a suitable catalyst. For example, the method comprises performing the reduction by catalytic hydrogenation at high pressure. The reaction is usually accomplished by shaking a mixture of the substrate and catalyst in a suitable solvent such as methanol, ethanol, aqueous dioxane or acetic acid under a high pressure atmosphere of hydrogen.

One particularly preferred embodiment of the process of the invention comprises reducing the compound of formula (7) to the epoxide of formula (1) by treatment with sodium borohydride in a mixture of water and methanol and keeping the temperature between $-5°$ C. and $5°$ C. Following completion of the reaction and appropriate work-up, the epoxide of formula (1) is obtained.

According to a further preferred embodiment of the invention, the resulting compound of formula (1) is isolated by crystallization from an appropriate solvent or mixture of solvents. Preferred solvents for the crystallization of the compound of formula (1) are polar protic and polar aprotic solvents such as alcohols, ketones or acetonitrile. If necessary an anti-solvent may be added. Preferred anti-solvents are among others water, hydrocarbons and ethers.

Still a further embodiment of the invention comprises converting the epoxide of formula (1) obtainable according to the process of the invention to Tulathromycin of the formula (2) above by reaction with n-propylamine. Methods and conditions for this conversion are disclosed, for example, in EP 0988310 or EP 1253153. Preferably, the epoxide of formula (1) is reacted with the n-propylamine in a $C_1$-$C_4$-alkanol solvent, for example in isobutanol, at elevated temperature, for example at a temperature of from 35 to $75°$ C.

The following examples further illustrate the invention without limiting it in any manner.

EXAMPLES

Example 1

50.0 g of Erythromycin A 9-(E)-oxime are added to 500 mL of methylene chloride. 16 mL of acetic anhydride are added dropwise and the mixture is maintained at room temperature for about 3 hours. The solution is added over 300 mL of a 10% aqueous solution of anhydrous potassium carbonate. 150 mL of methylene chloride are added, the mixture is agitated for 30 minutes and layers are separated. The organic layer is washed with 2×300 mL of a 10% aqueous solution of potassium carbonate and afterwards evaporated at reduced pressure until a solid is obtained. 60.1 g of the compound of formula (3), wherein $R_1$ and $R_2$ are each acetyl, are obtained (MS: 833, API-ES).

Example 2a 370 mL of DMSO are added to a suspension of 211 g of the compound of formula (3), wherein $R_1$ and $R_2$ are each acetyl, obtained according to Example 1 in about 1500 mL of methylene chloride. The mixture is cooled at $-70°$ C. and 73.6 mL of trifluoroacetic anhydride are added dropwise. The mixture is kept at $-65/-70°$ C. for 30 minutes and 165 mL of triethylamine are also added dropwise. The mixture is kept again at $-65/-70°$ C. for 35 minutes and added to 1500 mL of water in approximately 75 minutes. After separation, the organic layer is washed first with 1500 mL and secondly with 900 mL of water and evaporated at reduced pressure until a solid is obtained. 234.4 g of the compound of formula (4), wherein $R_1$ and $R_2$ are each acetyl, are obtained (MS: 831, API-ES).

Example 2b 16.5 g of the compound of formula (3), wherein $R_1$ and $R_2$ are each acetyl, according to Example 1 are added to 200 mL of methylene chloride. The mixture is distilled until an anhydrous media is obtained. 40 mL of DMSO are added and the mixture is cooled at $-70°$ C. 6.0 mL of trifluoroacetic anhydride are added dropwise and the mixture is kept afterwards at $-65/-70°$ C. for about 20 minutes. 13 mL of triethylamine are added dropwise and the mixture is kept at $-65/-75°$ C. for 45 minutes. 50 mL more of methylene chloride are added after completion of the reaction, and the whole mixture is finally added to 200 mL of water. After separation, the organic layer is washed with 2×200 mL of water and evaporated at reduced pressure until a solid is obtained. 14.9 g of the compound of formula (4), wherein $R_1$ and $R_2$ are each acetyl, are obtained.

A sample of 0.5 g of the previously obtained solid is added to 1.5 mL of acetone at room temperature. About 1 mL water is added until a precipitated solid is obtained and filtered. 0.38 g of pure compound of the formula (4), wherein $R_1$ and $R_2$ are each acetyl, are obtained.

Example 3a (a) 25.0 g of the compound of formula (4), wherein $R_1$ and $R_2$ are each acetyl, obtained according to Example 2a or 2b are added to 150 mL of methylene chloride. The mixture is distilled until an anhydrous media is obtained and the solution is kept to be used afterwards.
(b) 6.8 g of trimethylsulfonium bromide are added to 100 ml of THF. 32 mL are distilled to obtain an anhydrous media. The mixture is afterwards cooled to about −20° C. and 8.5 g of potassium tert-butoxide are added. The mixture is kept at −10/−20° C. during 75 minutes. The mixture is then cooled to −60° C./−70° C.
(c) The solution of the compound of the formula (4) according to (a) is slowly added to the reaction mixture according to (b) while maintaining the temperature at about −70° C. Following completion of the addition, the temperature is kept for 2 hours at about −70° C. An aqueous solution of ammonium chloride (12.7 g and 110 mL of water) is added in about 10 minutes and the temperature is left to rise up to 0/10° C. 50 mL of methylene chloride are added, the pH is adjusted to 10.5 with enough amount of NaOH 20% and layers are separated. The organic layer is washed with 100 ml of water. 50 mL of water are added to this organic layer and the mixture is distilled until precipitation is observed. 25 mL of water are added and the mixture is cooled at about 0/5° C. The precipitated solid is collected by filtration and washed with 2×25 mL of water. 9.8 g of the epoxide formula (5), wherein $R_1$ is acetyl and $R_2$ is hydrogen, are obtained (MS: 803, API-ES).

Example 3b (a) 85.0 g of the compound of formula (4), wherein $R_1$ and $R_2$ are each acetyl, obtained according to Example 2a or 2b are added to 425 mL of methylene chloride. The mixture is distilled until an anhydrous media is obtained and the solution is kept to be used afterwards.
(b) 27.9 g of trimethylsulfonium bromide are added to 340 ml of THF. 160 mL are distilled to obtain an anhydrous media. The mixture is afterwards cooled to about −20° C. and 34.8 g of potassium tert-butoxide are added. The mixture is kept at −10/−20° C. during 95 minutes. The mixture is then cooled to −60° C./−70° C.
(c) The previously prepared solution of compound of the formula (4) according to (a) is slowly added to the reaction mixture according to (b) while maintaining the temperature at about −70/−80° C. After the addition, the temperature is kept for about 1 hour at about −70° C. An aqueous solution of ammonium chloride (40.0 g and 400 mL of water) is added slowly and the temperature is left to rise up to 0/10° C. 60 mL of methylene chloride are added, the pH is adjusted to 10.2 with enough amount of NaOH 20% and layers are separated. The organic layer (about 470 mL) is washed with 2×400 ml of water and dried over anhydrous sodium sulfate.

60 mL of acetone are added to 100 mL of the previous organic layer. The mixture is distilled until removal of methylene chloride is completed. The mixture is cooled down to room temperature, filtered and washed with cooled acetone. 9.9 g of pure epoxide of the formula (5), wherein $R_1$ is acetyl and $R_2$ is hydrogen are obtained.

Example 4a

About 150 mL of methanol are added to 2.5 g of epoxide of the formula (5), wherein $R_1$ is acetyl and $R_2$ is hydrogen, until total solution is obtained. The mixture is left at room temperature for 4 hours. The mixture is then heated first to 50° C. and afterwards to 60/65° C. and left at that temperature until completion of reaction. The solvent is finally evaporated at reduced pressure until a solid is obtained (2.4 g compound of formula (6); MS: 761, API-ES).

Example 4b

About 1300 mL of methanol are added to 34.4 g of epoxide of the formula (5), wherein $R_1$ is acetyl and $R_2$ is hydrogen, until total solution is obtained. The mixture is left at room temperature for about 4 days until completion of reaction. The solvent is finally evaporated at reduced pressure until a solid is obtained (33.1 g of compound of formula (6)).

1.5 g of the previously obtained solid is added to a mixture of 15 mL of heptane and 5 ml of acetone. The mixture is heated at 65° C. and complete solution is obtained. The mixture is afterwards cooled very slowly at room temperature. The precipitated solid is filtered and washed with 5 mL of heptane. 0.7 g of pure compound of formula (6) are obtained.

Example 5a 100.8 g of compound of formula (6) are added to 442.0 g of acetone. 345.2 g of water are added slowly and the mixture is cooled to 0/5° C. 10 mL more of acetone are added. 33.6 g of p-toluenesulfonyl chloride are added portionwise maintaining the pH between 9.0-9.5 by simultaneous addition of an aqueous solution of NaOH 20%. The mixture is agitated during 45 minutes and left to stand and warm up to about 15/20° C. The mixture is agitated for 1 hour and 980 mL of water are slowly added afterwards. The mixture is adjusted to pH 11.0 by addition of enough amount of sodium hydroxide, agitated for 90 minutes, filtered and washed with 2×80 mL of water. 86.8 g of iminoether of formula (7) are obtained (MS: 743, API-ES).

Example 5b 15.8 g of compound of formula (6) are added to 69.6 g of acetone. 54.0 g of water are added slowly and the mixture is cooled to 0/5° C. 5.3 g of p-toluenesulfonyl chloride are added portionwise maintaining the pH between 9.0-9.5 by simultaneous addition of an aqueous solution of NaOH 20%. The mixture is agitated during 35 minutes and left to stand and warm up to about 15/20° C. The mixture is agitated for about 2 hours and 94 mL of water are slowly added afterwards. The mixture is adjusted to pH 10.5/11.0 by addition of enough amount of sodium hydroxide, agitated for 60 minutes, filtered and washed with 2×39 mL of water. 12.0 g of iminoether of formula (7) are obtained.

A mixture of 10.0 g of the previously obtained solid and 75 mL of acetone are refluxed until complete dissolution is obtained. The mixture is cooled to room temperature in 2 hours, cooled afterwards to about 15° C. and agitated during 30 minutes at this temperature. The precipitated solid is isolated by filtration and washed with 2×5 mL of acetone. 5.8 g of pure iminoether of formula (7) are obtained.

Example 6

45.0 g of iminoether of formula (7) are added to 105.0 g of methanol. 91.0 g of water are added slowly and the solution is cooled to −5/0° C. The pH is adjusted to 7.5 with HCl 18% and 28.5 g of 20% aqueous solution of sodium borohydride are added dropwise. The solution is agitated during 45 minutes keeping the temperature at −5/5° C. and the pH at about 7.5. 161 g of isopropyl acetate and 75 g of water are added in about 15 minutes and the pH is adjusted to 11.5 by addition of enough amount of sodium hydroxide. The mixture is heated to 30/40° C. and layers are separated. The aqueous layer is extracted with 30.7 g of isopropyl acetate. 169.6 g of water and 19.2 g of isopropyl acetate are added to the combined organic layers and the mixture is cooled to 0° C. The pH is adjusted to about 2.0 by addition of enough amount of HCl 18% and conditions are maintained for about 30 minutes. 45.0 g of N-methylglucamine are added in 2 portions, the pH is readjusted to 2.0 and the mixture is agitated for 45 minutes. The pH is adjusted to about 8.2 with enough amount of NaOH 20% and 14.7 g of isopropyl acetate are added. The mixture is heated to 35° C. and the pH is adjusted again to about 11.5 with enough amount of NaOH 20%. 170.0 g of isopropyl acetate are added and layers are separated. The aqueous layer is extracted with 100 mL more of isopropyl acetate. 250.0 g of water are added slowly to the organic layer and the mixture is cooled to 0° C. The pH is adjusted to 2.0 by addition of enough amount of HCl 18% and 30 g of isopropyl acetate and 30 g of water are added. pH and temperature conditions are maintained for about 30 minutes. 20.0 g of N-methylglucamine are added, the pH is readjusted to 2.0 and the mixture is agitated for 45 minutes. The mixture is afterwards heated to 30/40° C. and the pH is adjusted to about 11.5. pH and temperature conditions are maintained for about 30 minutes and layers are separated. The aqueous layer is extracted with 98.0 of isopropyl acetate and the combined organic layers are evaporated at reduced pressure until a solid is obtained (45.2 g of azalide of formula (1)).

The previously obtained solid is added to 230 mL of acetone. The mixture is heated and refluxed for about 10 minutes until complete dissolution is obtained and cooled afterwards to about 50° C. 400 mL of water are added dropwise and the mixture is slowly cooled to 15/20° C. The precipitated solid is filtered and washed with 57 mL of water and 57 mL of a mixture of acetone and water 2:3. 37.2 g of pure azalide of formula (1) are obtained (MS: 747, API-ES).

Example 7

(a) 150.4 g of Erythromycin A 9-(E)-oxime are added to 1500 mL of methylene chloride. 50 mL of acetic anhydride are added dropwise and the mixture is maintained at room temperature for 3 hours. 1000 mL of methylene chloride and 1000 mL of a 10% aqueous solution of sodium carbonate are added. The mixture is agitated for 30 minutes and layers are separated. The organic layer is washed with 2×1000 mL of a 10% aqueous solution of sodium carbonate. The resulting organic layer containing compound of formula (3), wherein $R_1$ and $R_2$ are each acetyl, is kept to be used in the following step.

(b) The crude product according to step (a) above is distilled until 25-30% of the starting volume is obtained. 300 mL of DMSO are added, the mixture is cooled at −70° C. and 56 mL of trifluoroacetic anhydride are added dropwise. The mixture is kept at −65/−70° C. for 30 minutes and 125 mL of triethylamine are also added dropwise. The mixture is kept again at −65/−70° C. for 30 minutes and added to 900 mL of water in approximately 1 hour. After separation, the organic layer is washed with 2×900 mL of water and evaporated at reduced pressure until a solid is obtained (160.4 g of compound of formula (4), wherein $R_1$ and $R_2$ are each acetyl).

(c) 160.4 g of the compound of formula (4), wherein $R_1$ and $R_2$ are each acetyl, obtained according to step (b) above are added to 700 mL of methylene chloride. The mixture is distilled until an anhydrous mixture is obtained and is kept to be used afterwards. 55.3 g of trimethylsulfonium bromide are added to 700 ml of THF. 420 mL are distilled to obtain an anhydrous media. The mixture is afterwards cooled at −20° C. and 60.2 g of potassium tert-butoxide are added portionwise. The mixture is kept at −10/−20° C. during 75 minutes. The mixture is then cooled to −60° C. and afterwards to −70/−80° C.

The previously prepared solution of the compound of formula (4) is slowly added to the reaction mixture maintaining the temperature at −70/−80° C. After the addition, the temperature is kept for 30 minutes at −65/−70° C. 200 mL of methylene chloride are added and the mixture is left to stand and warm up to about −40/−50° C. An aqueous solution of ammonium chloride (72.0 g in 650 mL) is added in about 15-30 minutes and the temperature is left to rise up to 10/20° C. Layers are separated. The organic layer is washed with 2×600 ml of water. The final organic layer is distilled until 20-30% of the starting volume is obtained and 600 mL of 2-propanol are added. The mixture is further distilled until start of precipitation is observed. The mixture is cooled down slowly to 10° C. and is left at that temperature for 90 minutes. The reaction mixture is filtered and washed with 60 mL of cooled 2-propanol to obtain 117.1 g of the epoxide of formula (5), wherein $R_1$ is acetyl and $R_2$ is hydrogen.

(d) 117.1 g of the epoxide obtained according to step (c) are added to 4500 mL of methanol. The mixture is left with agitation for 7 days at room temperature and evaporated at reduced pressure until a solid is obtained (109.8 g of the compound of formula (6)).

(e) 109.8 g of the compound of formula (6) obtained according to step (d) are added to 485.4 g of acetone. 378.7 g of water are added slowly and the mixture is cooled to −5/5° C. 36.3 g of p-toluenesulfonyl chloride are added portionwise maintaining the pH between 9.0-9.5 by simultaneous addition of an aqueous solution of NaOH 20%. The mixture is agitated during 40 minutes and left to stand and warm up to about 15/20° C. The mixture is agitated for 3 more hours and 1076 mL of water are slowly added afterwards. The mixture is adjusted to pH 11.0 by addition of enough amount of sodium hydroxide, agitated for 1 hour, filtered and washed with 275 mL of cooled water. 101.4 g of the iminoether of formula (7) are obtained.

(f) 101.4 g of the iminoether of formula (7) obtained according to step (e) are added to 236.8 g of methanol. 196.7 g of water are added slowly and the solution is cooled to −5/5° C. The pH is adjusted to 7.5 with HCl 18% and 63.6 g of 20% aqueous solution of sodium borohydride are added dropwise. The solution is agitated during 30 minutes keeping the temperature at −5/5° C. and the pH at about 7.5. 357.3 g of isopropyl acetate and 169.6 g of water are added in 15 minutes and the pH is adjusted to 11.5 by addition of enough amount of sodium hydroxide. The mixture is heated to 25/30° C. and layers are separated. The aqueous layer is discarded. 382.9 g of water are added to the organic layer and the mixture is cooled to 0° C. The pH is adjusted to 2.0 by addition of enough amount of HCl 18% and conditions are maintained for about 30 minutes. 101.5 g of N-methylglucamine are added in 2 portions, the pH is readjusted to 2.0 and the mixture is agitated for 45 minutes. 394.2 g of isopropyl acetate are added, the pH is adjusted to about 11.0 with sodium hydroxide 20% and layers are separated. 564.4 g of water are added to the organic layer and the mixture is cooled to 0° C. The pH is adjusted to 2.0 by addition of enough amount of HCl 18% and conditions are maintained for about 30 minutes. 33.9 g of N-methylglucamine are added, the pH is readjusted to 2.0 and the mixture is agitated for 45 minutes. The pH is first adjusted to about 8.5 and to about 11.0 after warming the mixture at 25/30° C. Layers are separated and the organic layer is evaporated at low pressure until a solid is obtained (90.4 g of the azalide of formula (1)).

Example 8

90.4 g of the azalide of formula (1) obtained according to example 6 or 7 are added to 900 mL of isobutanol. 100 mL of N-propylamine are added while the mixture is heated at 55/65° C. The temperature is maintained for 15 hours with further additions of N-propylamine, if required, until completion of the reaction. Finally, the solvent is evaporated at low pressure until a solid is obtained (95.7 g of Tulathromycin of formula (2)).

The invention claimed is:

1. Process for the manufacture of a compound of formula (1)

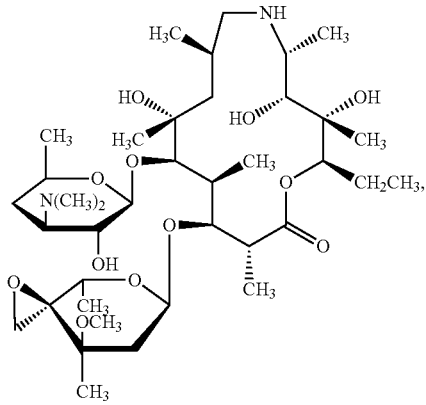

comprising the steps of:
(i) protecting the hydroxyl group in the C-2' and, optionally, the C-9 oxime group of erythromycin A 9-(E)-oxime to obtain a compounds of formula (3)

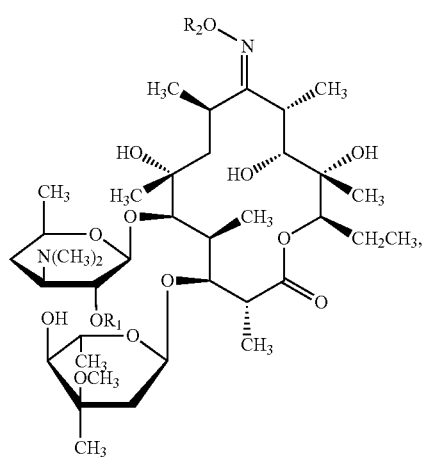

wherein $R_1$ is a hydroxyl protecting group and $R_2$ is hydrogen or an oxime protecting group;

(ii) oxidizing the compound of formula (3) in the presence of an oxidizing agent in order to obtain a compound of formula (4)

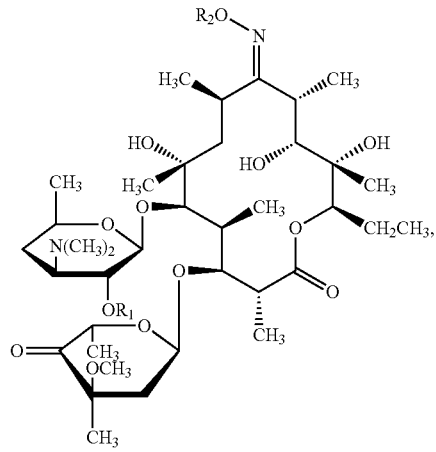

wherein $R_1$ and $R_2$ are as defined above;
(iii) converting the compound of formula (4) to the corresponding epoxide of formula (5)

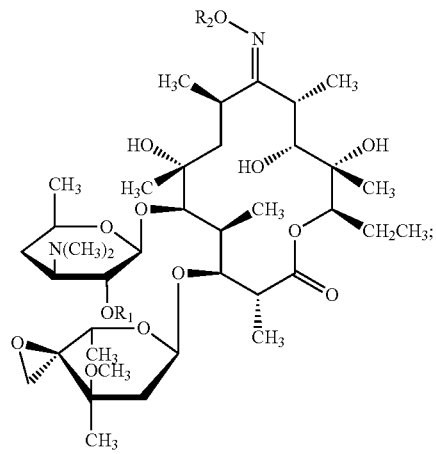

wherein $R_1$ and $R_2$ are each as defined above;
(iv) removing the protecting group $R_1$ and optionally $R_2$ of the compound of formula (5) to yield the compound of formula (6)

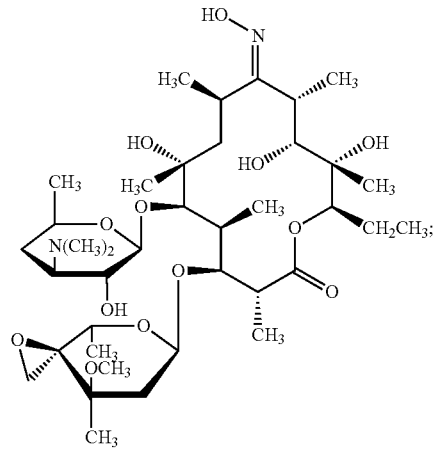

(v) subjecting the oxime of formula (6) to a Beckmann rearrangement in order to obtain the corresponding 6,9-iminoether of formula (7)

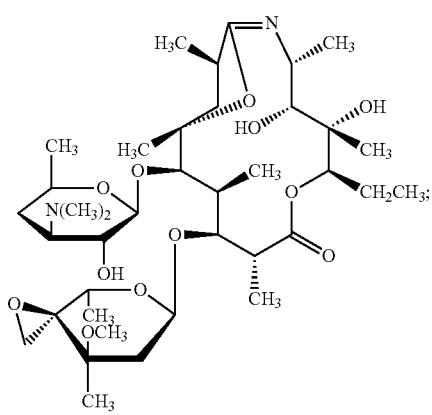

and (vi) reducing the iminoether of formula (7) to obtain the epoxide of formula (1).

2. The process according to claim 1, wherein the oxidation of the compound of formula (3) in step (ii) is performed with dimethylsulfoxide which is activated by trifluoroacetic anhydride, oxalyl chloride, a polyphosphoric acid, a pyridine-$SO_3$ complex or acetic anhydride.

3. The process of claim 1, wherein $R_1$ and $R_2$ in formulae (3) and (4) are both $C_2$-$C_4$-alkanoyl.

4. The process of claim 1, wherein the preparation of the epoxide of formula (5) according to step (iii) comprises reacting the carbonyl group in the C-4" position with a sulfonium methylide ion.

5. The process of clairnl, wherein the removal of the protecting group of $R_1$ and optionally $R_2$ is carried out by a treatment with a $C_i$-$C_4$-alkanol.

6. The process of claim 1, wherein the preparation of the compound of formula (7) according to step (v) is performed by reacting the oxime of formula (6) with a sulfonic acid derivative.

7. The process of claim 1, wherein the reduction of the iminoether of formula (7) according to step (vi) is carried out with a complex metal hydride as reducing agent.

8. A process for the manufacture of Tulathromycin, which comprises:
(i) protecting the hydroxyl group in the C-2' and, optionally, the C-9 oxime group of erythromycin A 9-(E)-oxime to obtain a compound of formula (3)

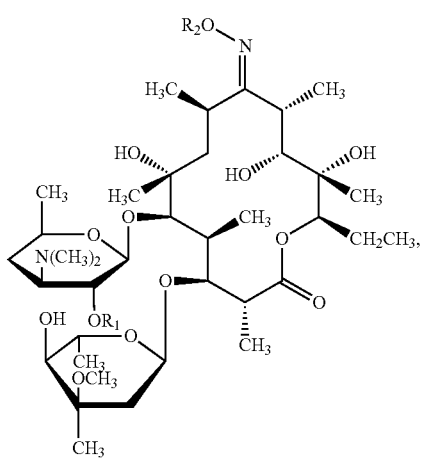

wherein $R_1$ is a hydroxyl protecting group and R is hydrogen or an oxime protecting group;

(ii) oxidizing the compound of formula (3) in the presence of an oxidizing agent in order to obtain a compound of formula (4)

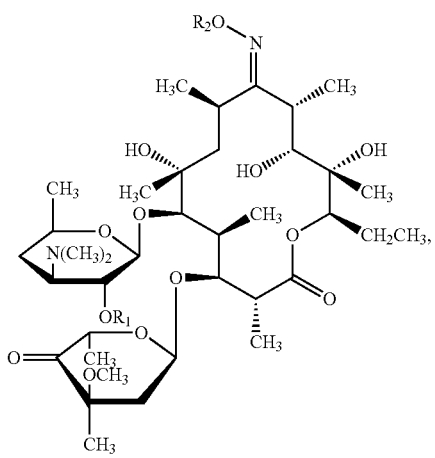

wherein $R_1$ and R are as defined above;

(iii) converting the compound of formula (4) to the corresponding epoxide of formula (5)

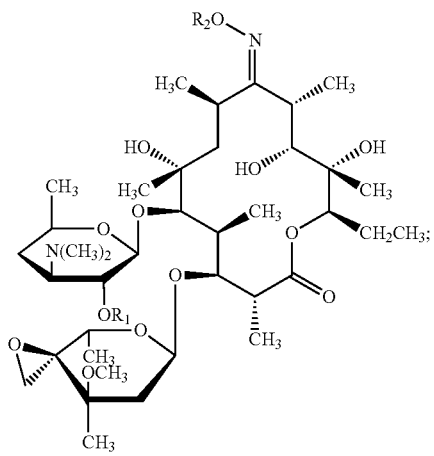

wherein $R_1$ and R are each as defined above;

(iv) removing the protecting group $R_1$ and optionally $R_2$ of the compound of formula (5) to yield the compound of formula (1)

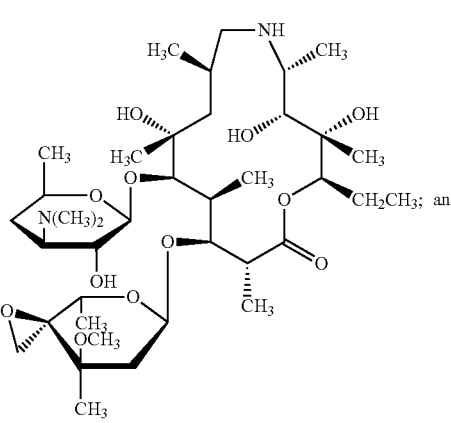

(v) reacting the compound of formula (1) with n-propylamine.

9. The process of claim 2 wherein the dimethylsulfoxide is activated by trifluoroacetic anhydride.

10. The process of claim 3 wherein the $C_2$-$C_4$-alkanoyl is acetyl.

11. The process of claim 5 wherein the $C_1$-$C_4$-alkanol is methanol.

12. The process of claim 6 wherein the sulfonic acid derivative is toluenesulfonyl chloride.

* * * * *